United States Patent [19]

Collins

[11] Plant 4,758

[45] Aug. 18, 1981

[54] FLOWERING CRABAPPLE TREE

[75] Inventor: William H. Collins, Circleville, Ohio

[73] Assignee: American Garden Cole, Inc., Circleville, Ohio

[21] Appl. No.: 146,781

[22] Filed: May 5, 1980

[51] Int. Cl.[3] ..... A01H 5/00

[52] U.S. Cl. ..... Plt./34

[58] Field of Search ..... Plt./34

*Primary Examiner*—James R. Feyrer

*Attorney, Agent, or Firm*—Maky, Renner, Otto & Boisselle

[57] ABSTRACT

A new and distinct variety of flowering crabapple tree, characterized by its rapid growth habit of numerous, compact, sturdy, upright branches, branching freely at the base; attractive purplish red foliage appearing resistant to scab and mildew; and sparse but pleasing purplish red flowers and dark red to deep purple fruits.

4 Drawing Figures

1

The present invention or discovery relates to a new and distinct variety of Malus sp., commonly known as flowering crabapple tree, having an unusual growth habit, which originated as a seedling selected from a large planting of flowering crabapple seedlings made by me.

This new variety of flowering crabapple tree is a shrub or small tree having numerous lower branches emerging from the trunk and growing almost vertical. All newly formed branches also show the vertical growth habit, giving an overall, shrubby, hedge-like appearance. This hedge-like habit forms rapidly due to the very vigorous young growth of such plant. With the removal of lower branches, a small tree with a compact, fastigiate head can be readily produced. The plant has an attractive purplish red foliage, which appears resistant to scab and mildew. The flowers of this new variety are of relatively short duration and scattered, and the fruits are also produced sparingly and are small and quite well hidden by the foliage.

The novel and distinctive features of this new variety are accordingly considered to be, in combination:

1. The free branching, upright, compact hedge-like growth of the plant, qualifying it as an outstanding hedge and screening plant, reaching an estimated mature height of 10 to 12 feet.
2. Branching freely at the base overcomes any tendency for legginess.
3. Its rapid growth rate.
4. The fact that little maintenance is required to assure its narrow, upright compact growth habit.
5. The attractive purplish red foliage, appearing resistant to scab and mildew.
6. The sparse, but pleasing purplish red flowers and dark red to deep purple fruit.
7. The fact that with the removal of the lower branches a small tree, with a compact, fastigiate head can be produced readily.

My new flowering crabapple tree has been propagated asexually at Circleville, Ohio, by budding, and I have found that the above-indicated desirable characteristics are consistently perpetuated in the progeny. Bud-propagated progeny of this new variety are now growing at Circleville, Ohio, and demonstrate the same novel characteristics. The original parent specimen was a seedling grown by me at Circleville, Ohio, and such original plant specimen was discovered and selected by me in a large plantation of crabapple tree seedlings.

2

Referring now more particularly to the drawing.

Figure 1:
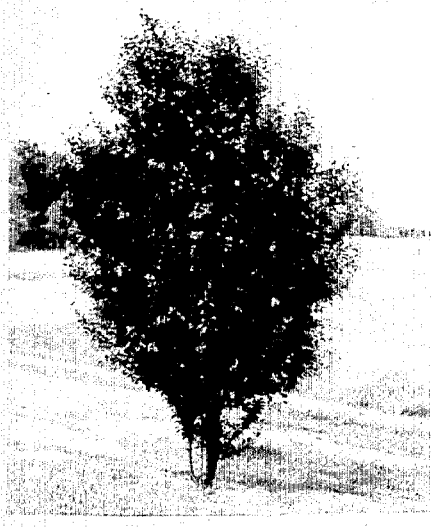
FIG. 1 shows my new flowering crabapple tree in full summer foliage.
Figure 2:
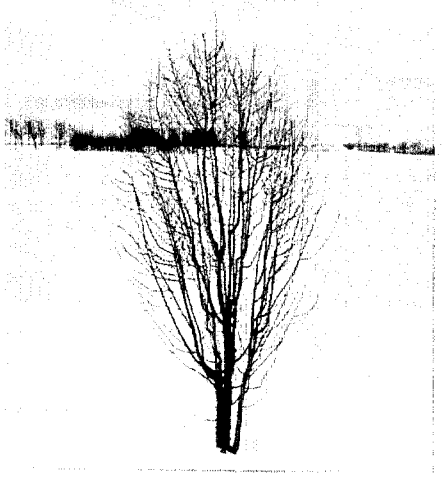
FIG. 2 shows such plant in winter after dropping of the foliage showing its compact, upright form.
Figure 3:
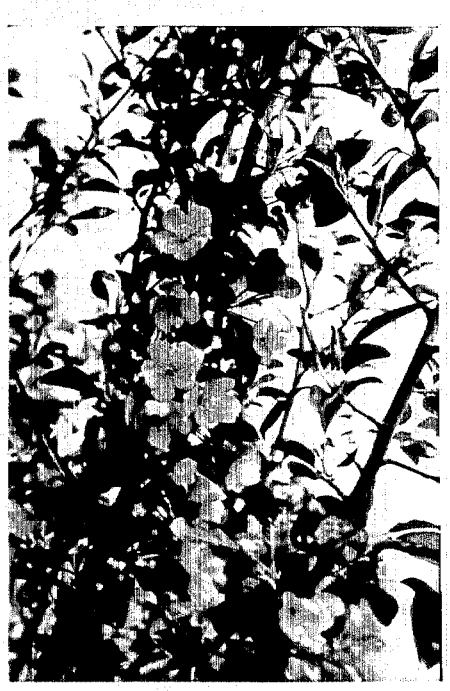
FIG. 3 shows the flowers of such plant.
Figure 4:
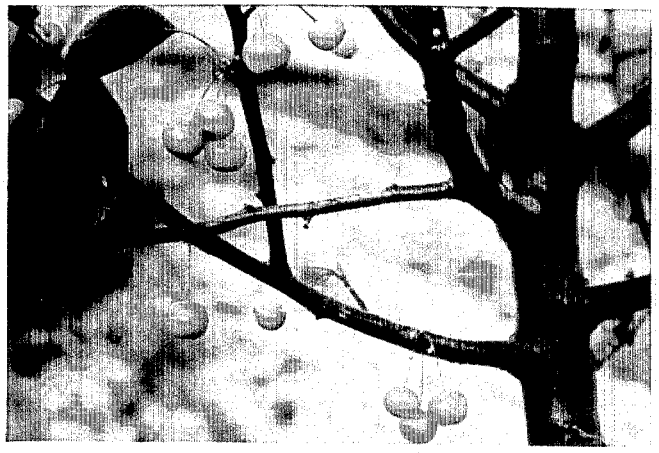
FIG. 4 shows the fruits of such plant.

The following is a specific description of such new variety, the color terminology and reference to the buds, flowers, and foliage being based on the Nickerson Color Fan approved by the American Horticultural Society.

The original plant, at about 10 years old, has a basal trunk diameter of 4½ inches, and both such original plant and subsequent progeny show numerous lower branches emerging from the trunk and growing almost vertical. All newly formed branches also show the vertical growth habit, giving an overall, shrubby, hedge-like appearance. The hedge-like habit forms rapidly due to the vigorous young growth.

The numerous, compact, sturdy, upright branches and branchlets are glabrous at the base but hairy near the tips of current growth. The texture of the branchlets is typical of Malus, medium to somewhat stout. Current twig growth is purplish in color with prevalent lenticels.

Twig buds are oval to semi-pointed, relatively small, with about two pairs of hairy scales. Scales are reddish-purple with grayish hairs.

Medial, exposed leaves on current shoots are oval to oval-elongated, ranging from approximately 6½ to 9 cm. in length and 4½ to 6 cm. wide, at the widest center portion of the leaf. Leaves are slightly hairy above, especially along the midrib; and quite hairy below with midrib densely hairy. The petioles are approximately 2 to 2½ cm. long. Leaves are finely serrate, with 4 to 6 pairs of main veins, abruptly accuminate at the tip, and rounded at the base. Stipules are prominent on leaves of current growth, foliate, and up to 1 cm. long. Stipules are usually wanting on older leaves. Shaded leaves are much smaller and narrower, slightly hairy above and below, with stipules usually wanting. Petioles on shaded leaves may exceed 2½ cm. in length.

Exposed, mature leaves are deep purplish-red (10 RP 3/10, Nickerson Color Fan, American Horticultural Society) above, moderate olive green (5.0 GY 4/3 to 7.5 GY 4/4) below. Shade leaves are grayish olive green (2.5 GY 3/1 to 5.0 GY 3/2) above, with occasional purplish cast.

Flowers of this new cultivar, produced in mid to late April, are of relative short duration. Young plants produce only scattered, single flowers. Flowering habit varies greatly from tree to tree; such flowers often being mal-formed or irregular in shape, small, with 4 to 5 petals that are often cupped. The petals vary from 12 to 20 mm. in length, mostly with a rounded tip. Flower pedicels are 2¾ to 3½ cm. long.

The inside petal color is strong, purplish red (7.5 RP 5/12 to 10 RP 4/12). Color of the back of the petal is deep, purplish red (10 RP 3/10) to strong, purplish red (7.5 RP 4/11).

Fruits are produced sparingly, although varying considerably from plant to plant, and are small and quite well hidden by the foliage. Fruits are borne singly or in clusters of 3, 4 or 5, with each fruit being approximately 1.0 to 1.3 cm. long and 1.2 to 1.5 cm. broad. Fruit stems vary from 2.2 to 3.0 cm. long. Fruits are concave at the stem end, rounded at the base, with calyx usually absent. Fruits ripen in late September, are of firm texture, persisting until late fall or winter. The exposed, sunny side of the fruits is glossy, dark red (2.5 R 3/7 to 5 R 3/7), to deep purple (2.5 R 6/11). The shaded side of the fruits varies from strong, yellowish pink (5 R 7/9) to moderate red (2.5 R 4/10), occasionally to strong red (2.5 R 5/12).

Because of its free branching, upright, compact hedge-like growth habit, this new variety is particularly suited for use as a hedge and screening plant. Also, with the removal of lower branches, a small tree with a compact, fastigiate head can be readily produced.

I claim:

1. A new and distinct variety of flowering crabapple tree, Malus sp., substantially as described and illustrated, characterized by its rapid growth habit of numerous, compact, sturdy, upright branches, branching freely at the base; attractive purplish red foliage, appearing resistant to scab and mildew; and sparse but pleasing purplish red flowers and dark red to deep purple fruits.

* * * * *